(12) United States Patent
Zou et al.

(10) Patent No.: US 8,396,185 B2
(45) Date of Patent: Mar. 12, 2013

(54) METHOD OF FAST CURRENT MODULATION IN AN X-RAY TUBE AND APPARATUS FOR IMPLEMENTING SAME

(75) Inventors: Yun Zou, Clifton Park, NY (US); Brian Lounsberry, Thiensville, WI (US); Carey Shawn Rogers, Brookfield, WI (US); Sergio Lemaitre, Whitefish Bay, WI (US); Xiaoye Wu, Rexford, NY (US); Jizhong Chen, Medford, MA (US); Floribertus P. Heukensfeldt Jansen, Ballston Lake, NY (US)

(73) Assignee: General Electric Company, Niskayuna, NY (US)

( * ) Notice: Subject to any disclaimer, the term of this patent is extended or adjusted under 35 U.S.C. 154(b) by 222 days.

(21) Appl. No.: 12/778,756

(22) Filed: May 12, 2010

(65) Prior Publication Data

US 2011/0280363 A1    Nov. 17, 2011

(51) Int. Cl.
 H05G 1/08 (2006.01)
 H05G 1/32 (2006.01)
 H05G 1/56 (2006.01)
 H01J 35/06 (2006.01)
 H01J 35/14 (2006.01)
(52) U.S. Cl. ........... 378/16; 378/112; 378/115; 378/136
(58) Field of Classification Search .................... 378/16, 378/91, 92, 101, 109–116, 119, 121, 134, 378/136, 138, 210
See application file for complete search history.

(56) References Cited

U.S. PATENT DOCUMENTS

| | | | | |
|---|---|---|---|---|
| 3,244,878 A * | 4/1966 | Stevenson et al. | | 378/41 |
| 3,250,916 A * | 5/1966 | Rogers | | 378/41 |
| 3,432,658 A * | 3/1969 | Quinn | | 378/41 |
| 4,065,689 A | 12/1977 | Pleil | | |
| 4,637,040 A * | 1/1987 | Sohval et al. | | 378/9 |
| 5,065,420 A * | 11/1991 | Levene | | 378/137 |
| 5,485,494 A | 1/1996 | Williams et al. | | |
| 5,617,464 A | 4/1997 | Mika et al. | | |
| 5,625,662 A | 4/1997 | Toth et al. | | |
| 5,633,907 A * | 5/1997 | Gravelle et al. | | 378/121 |
| 5,748,701 A | 5/1998 | Mika et al. | | |
| 5,930,331 A | 7/1999 | Rentzepis et al. | | |
| 6,215,850 B1 | 4/2001 | Blake et al. | | |
| 6,385,280 B1 | 5/2002 | Bittl et al. | | |
| 6,816,573 B2 | 11/2004 | Hirano et al. | | |
| 7,079,623 B2 | 7/2006 | Heuft et al. | | |
| 7,085,351 B2 | 8/2006 | Lu et al. | | |
| 7,110,500 B2 | 9/2006 | Leek | | |
| 7,151,818 B1 | 12/2006 | Hanington et al. | | |
| 7,203,268 B2 | 4/2007 | Yahata | | |
| 7,529,344 B2 * | 5/2009 | Oreper | | 378/134 |
| 2006/0115050 A1 | 6/2006 | Resnick | | |
| 2010/0104062 A1 * | 4/2010 | Wu et al. | | 378/19 |
| 2011/0188625 A1 * | 8/2011 | Roshi et al. | | 378/4 |

FOREIGN PATENT DOCUMENTS

WO    02073650 A2    9/2002

* cited by examiner

*Primary Examiner* — Anastasia Midkiff
(74) *Attorney, Agent, or Firm* — Marie-Claire B. Maple

(57) ABSTRACT

An X-ray tube includes a target and a cathode assembly. The cathode assembly includes a first filament configured to emit a first beam of electrons toward the target, a first gridding electrode coupled to the first filament, a second filament configured to emit a second beam of electrons toward the target, and a second gridding electrode coupled to the second filament.

25 Claims, 6 Drawing Sheets

METHOD OF FAST CURRENT MODULATION IN AN X-RAY TUBE AND APPARATUS FOR IMPLEMENTING SAME

BACKGROUND OF THE INVENTION

Embodiments of the invention relate generally to x-ray imaging devices and, more particularly, to an X-ray tube having an improved control of electron beam emission, and thus, of X-ray generation.

X-ray systems typically include an X-ray source or tube, a detector, and a support structure for the X-ray tube and the detector. In operation, an imaging table, on which the object is positioned, is located between the X-ray tube and the detector. The X-ray tube typically emits radiation, such as X-rays, toward the object. The radiation typically passes through the object on the imaging table and impinges on the detector. As radiation passes through the object, internal structures of the object cause spatial variations in the radiation received at the detector. The data acquisition system reads the signals received in the detector, and the system translates the radiation variations into an image, which may be used to evaluate the internal structure of the object. One skilled in the art will recognize that the object may include, but is not limited to, a patient or subject in a medical imaging procedure and an inanimate object as in, for instance, a package in an X-ray scanner or computed tomography (CT) package scanner. Hereinafter, the terms "subject" and "object" shall include anything capable of being imaged with X-rays.

Typically, in an imaging system such as a computed tomography (CT) imaging system, an X-ray source emits a fan-shaped or cone-shaped beam toward an object, such as a patient or a piece of luggage. The beam, after being attenuated by the object, impinges upon an array of radiation detectors. The intensity of the attenuated beam radiation received at the detector array is typically dependent upon the attenuation of the X-ray beam by the subject. Each detector element of the detector array produces a separate electrical signal indicative of the attenuated beam received by each detector element. The electrical signals are transmitted to a data processing system for analysis, which ultimately are used to produce an image.

X-ray detectors typically include a collimator for collimating X-ray beams received at the detector, scintillator adjacent the collimator for converting X-rays to light energy, and photodiodes for receiving the light energy from the adjacent scintillator and producing electrical signals therefrom. Typically, each scintillator of a scintillator array converts X-rays to light energy. Each scintillator discharges light energy to a photodiode adjacent thereto. Each photodiode detects the light energy and generates a corresponding electrical signal. The outputs of the photodiodes are then transmitted to the data processing system for image reconstruction.

X-ray tubes typically include an anode structure or target for the purpose of distributing heat generated at a focal spot. An X-ray tube cathode provides an electron beam from an emitter that is accelerated using a high voltage applied across a cathode-to-anode vacuum gap to produce X-rays upon impact with the anode. The area where the electron beam impacts the anode is often referred to as the focal spot. Typically, the cathode includes one or more filaments positioned within a cup for emitting electrons as a beam to create a high-power large focal spot or a high-resolution small focal spot, as examples. Imaging applications may be designed that include selecting either a small or a large focal spot having a particular shape, depending on the application.

In the following paragraphs a more detailed description will be provided of a CT system that implements the improved method of electron beam control that is the subject of this invention. However, it is to be understood that the invention is not limited to CT systems but can be applied to all types of imaging systems that include one or more X-ray tubes.

A CT imaging system may include an energy discriminating, multi energy, or dual energy capability. Techniques to obtain the measurements may include scanning with two distinctive energy spectra and detecting photon energy according to energy deposition in the detector. Systems may provide energy discrimination and material characterization based on low-energy and high-energy portions of incident X-rays. In a given energy region of medical CT, two physical processes dominate the x-ray attenuation: (1) Compton scatter and the (2) photoelectric effect. Thus, as known in the art, detected signals from two energy regions provide sufficient information to resolve energy dependence of the material being imaged and determine a relative composition of an object composed of two hypothetical materials.

A conventional third generation CT system may acquire projections sequentially at different peak kilovoltage (kVp) levels, which changes the peak and spectrum of energy of the incident photons comprising the emitted x-ray beams. Two scans are acquired—either (1) back-to-back sequentially in time where the scans include two rotations around the subject, or (2) interleaved as a function of the rotation angle requiring one rotation around the subject, in which the tube operates at, for instance, 80 kVp and 140 kVp potentials. When scanning sequentially, data obtained may be misregistered because of slight motion of the object between acquisitions. However, high frequency generators have made it possible to switch the tube voltage or potential of the X-ray source on alternating views. As a result, data for two energy sensitive scans may be obtained in a temporally interleaved fashion rather than in two separate scans made several seconds apart.

Thus, it is desirable to deliver microsecond or sub-microsecond current modulation of the electron beam and/or gridding in some imaging applications such that temporally interleaved scanning data may be obtained. Some technologies are capable of increasing or decreasing electron beam current, but such technologies achieve current modulation by changing an emitter temperature and thus the emitted beam current. Such current modulation processes are slow due to the thermal time constant of the emitter. That is, due to thermal mass of the filament it is not possible to achieve significant current modulation with this approach on a microsecond timescale.

To achieve a fast current response time, gridding technologies may be used to control electron beam operation electrostatically and modulate current, either via an intercepting or a non-intercepting grid. Typically, however, if high voltage is increased or decreased, the current will correspondingly increase or decrease as a consequence of respectively higher or lower electric fields at the emitter surface, which is a trend opposite that which is typically desired. That is, for an increased voltage it is typically desirable to have a decreased current, and vice versa. The higher current at lower voltage is desired to obtain sufficient X-ray flux at the detector surface, since the X-ray attenuation coefficient of materials decreases with increasing energy of the incident X-ray beam.

For a low tube voltage operation it is typically desirable to have a high current or tube mA, which in some applications is 1000 mA or greater at 80 kV, as an example. Correspondingly, it is typically desirable to have a low current or tube mA, 750 mA or less, at 140 kV. In today's tube, it is possible to achieve high emission by increasing filament temperature. However, as stated, this is a slow process and the temporal response of the temperature change of a filament is in the range of milliseconds. Second, increasing the temperature of the filament may curtail or limit filament life. Thus, for a fast kV switching operation, system operation and life requirements may limit the performance at desired current during low tube voltage operation of the fast kV switching operation.

Therefore, it would be desirable to have an apparatus and method capable of microsecond current modulation of an electron beam in an X-ray imaging device, while achieving high current emission without compromising emitter life.

BRIEF DESCRIPTION

Embodiments of the invention provide an apparatus and method that overcome the aforementioned drawbacks by providing for modulating current of an electron beam in an X-ray imaging device.

In accordance with one aspect of the invention, an X-ray tube includes a target and a cathode assembly. The cathode assembly includes a first filament configured to emit a first beam of electrons toward the target, a first gridding electrode coupled to the first filament, a second filament configured to emit a second beam of electrons toward the target, and a second gridding electrode coupled to the second filament.

In accordance with another aspect of the invention, a method of multi-energy imaging includes determining a first X-ray tube current based on a first X-ray tube voltage level, and a second X-ray tube current based on a second X-ray tube voltage level, applying a first filament current to a first filament, and a second filament current to a second filament, alternatingly applying the first X-ray tube voltage level and the second X-ray tube voltage level to a cathode assembly that houses the first filament and the second filament, selectively applying first and second gridding voltages to respective first and second gridding electrodes during application of the first and second X-ray tube voltage levels across a cathode-anode gap such that emission from the first and second filaments is separately controllable respective to the tube voltage, acquiring imaging information from X-rays generated at a focal spot, and generating an image using the imaging information.

In accordance with yet another aspect of the invention, an imaging system includes a gantry having an opening for receiving an object to be scanned, and an X-ray source coupled to the gantry and configured to project X-rays through the opening. The X-ray source includes a target and a cathode assembly. The cathode assembly includes a first filament configured to emit a first electron beam toward the target, a first gridding electrode coupled to the first filament, a second filament configured to emit a second electron beam toward the target, and a second gridding electrode coupled to the second filament. The system includes a controller configured to acquire imaging data from X-rays generated by electrons emitted from the cathode assembly during energization of the cathode assembly to a first tube voltage level and a second tube voltage level, and generate an image using the acquired imaging data.

Various other features and advantages will be made apparent from the following detailed description and the drawings.

BRIEF DESCRIPTION OF THE DRAWINGS

The drawings illustrate one or more embodiments presently contemplated for carrying out embodiments of the invention.

In the drawings.

DETAILED DESCRIPTION

Applications of X-ray sources comprise imaging, medical, security, and industrial inspection applications for use in X-ray imaging systems.

The operating environment of the present invention is described with respect to a sixty-four-slice computed tomography (CT) system. However, it will be appreciated by those skilled in the art that the present invention is equally applicable for use with other multi-slice configurations. The invention is not limited to CT systems but can be applied to all types of imaging systems that include one or more X-ray tubes. The present invention will be described with respect to a "third generation" CT scanner, but is equally applicable with other CT systems.

Figure 1:
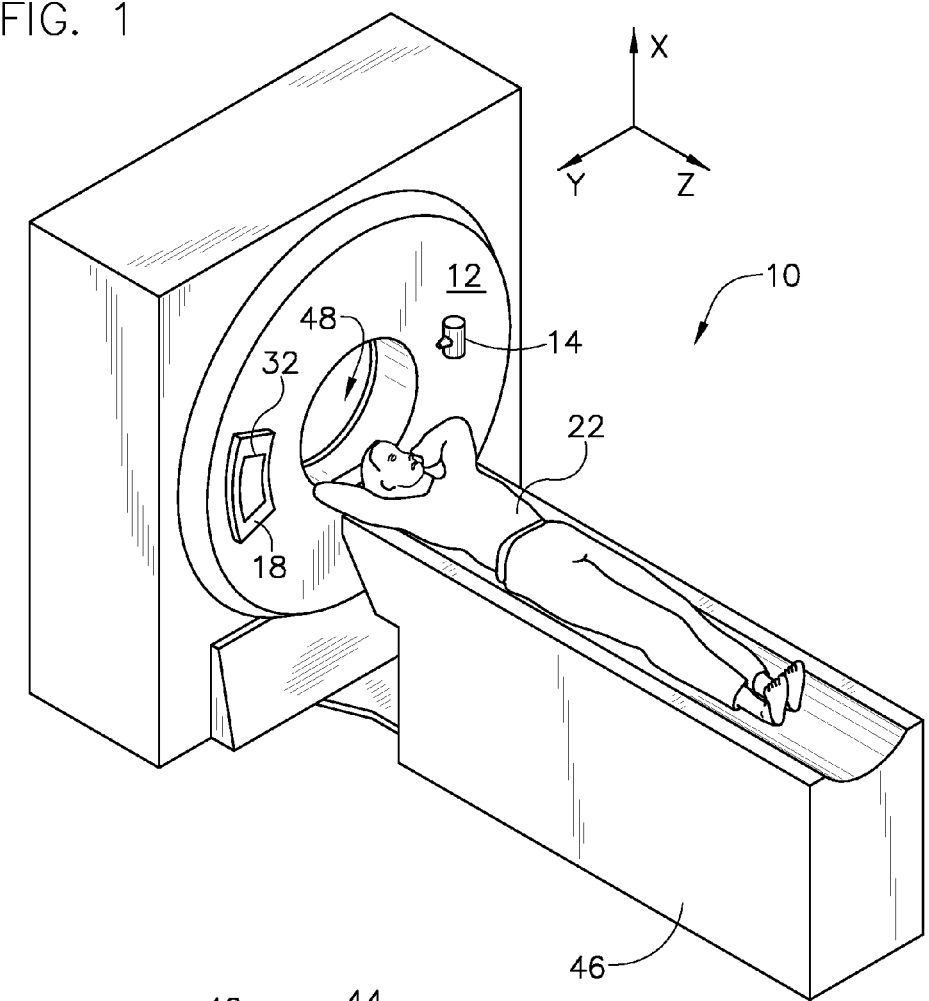
FIG. 1 is a pictorial view of a CT imaging system incorporating embodiments of the invention.
Figure 2:
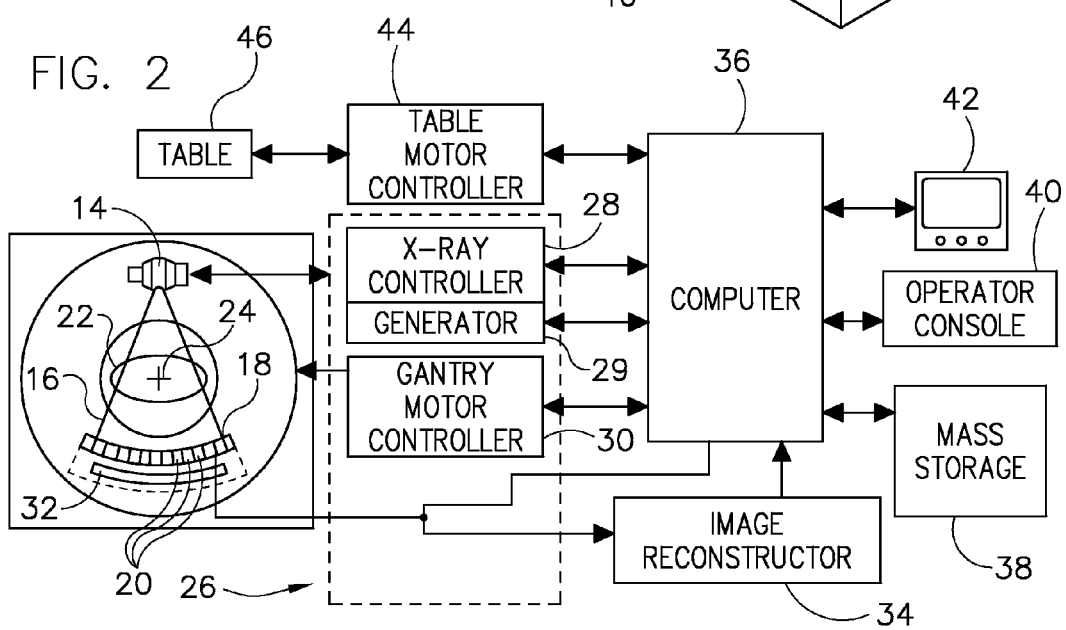
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an X-ray source 14 that projects a beam of X-rays 16 toward a detector assembly or collimator 18 on the opposite side of the gantry 12. In embodiments of the invention, X-ray source 14 includes either a stationary target or a rotating target. Detector assembly 18 is formed by a plurality of detectors 20 and data acquisition systems (DAS) 32. The plurality of detectors 20 sense the projected X-rays that pass through a medical patient 22, and DAS 32 converts the data to digital signals for subsequent processing. Each detector 20 produces an analog electrical signal that represents the intensity of an impinging X-ray beam and hence the attenuated beam as it passes through the patient 22. During a scan to acquire X-ray projection data, gantry 12 and the components mounted thereon rotate about a center of rotation 24.

Rotation of gantry 12 and the operation of X-ray source 14 are governed by a control mechanism 26 of CT system 10. Control mechanism 26 includes an X-ray controller 28 and generator 29 that provides power and timing signals to the X-ray source 14 and a gantry motor controller 30 that controls the rotational speed and position of gantry 12. An image reconstructor 34 receives sampled and digitized X-ray data from DAS 32 and performs high speed reconstruction. The reconstructed image is applied as an input to a computer 36 which stores the image in a mass storage device 38.

Computer 36 also receives commands and scanning parameters from an operator via console 40 that has some form of operator interface, such as a keyboard, mouse, voice activated controller, or any other suitable input apparatus. An associated display 42 allows the operator to observe the reconstructed image and other data from computer 36. The operator supplied commands and parameters are used by computer 36 to provide control signals and information to DAS 32, X-ray controller 28 and gantry motor controller 30. In addition, computer 36 operates a table motor controller 44 which controls a motorized table 46 to position patient 22 and gantry 12. Particularly, table 46 moves patients 22 through a gantry opening 48 of FIG. 1 in whole or in part.

Figure 3:
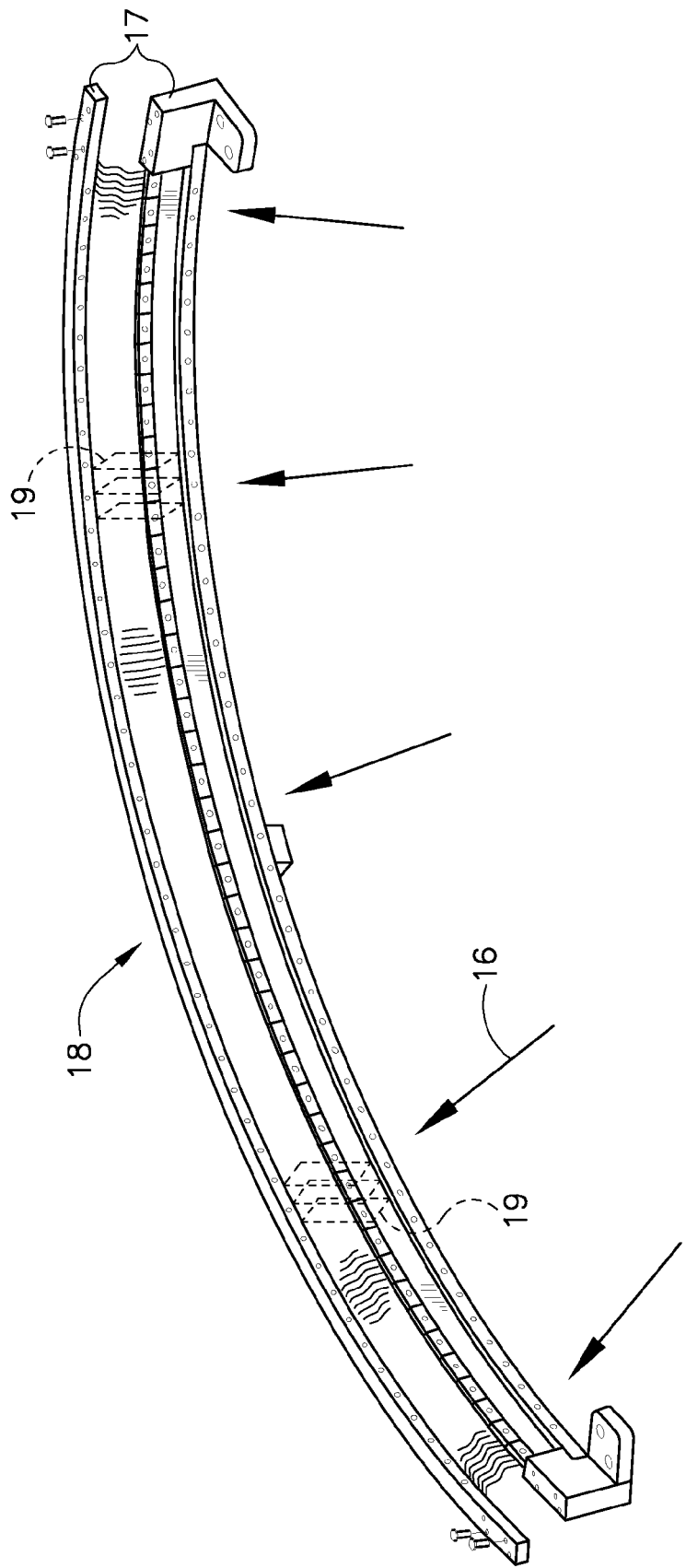
FIG. 3 is a perspective view of one embodiment of a CT system detector array.

As shown in FIG. 3, detector assembly 18 includes rails 17 having collimating blades or plates 19 placed therebetween. Plates 19 are positioned to collimate X-rays 16 before such beams impinge upon, for instance, detector 20 of FIG. 4 positioned on detector assembly 18. In one embodiment, detector assembly 18 includes 57 detectors 20, each detector 20 having an array size of 64×16 of pixel elements 50. As a result, detector assembly 18 has 64 rows and 912 columns (16×57 detectors) which allows 64 simultaneous slices of data to be collected with each rotation of gantry 12.

Figure 4:
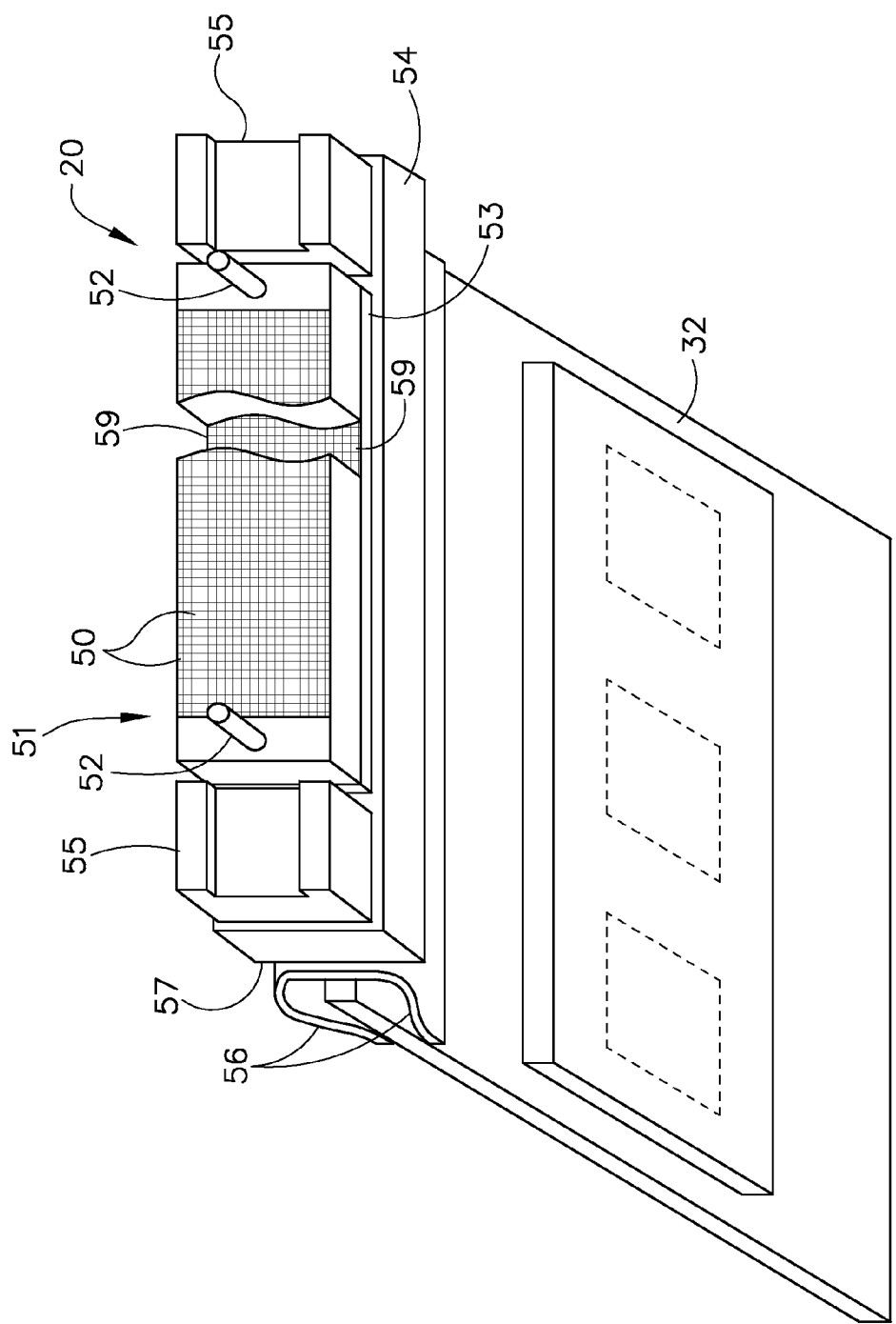
FIG. 4 is a perspective view of one embodiment of a detector.

Referring to FIG. 4, detector 20 includes DAS 32, with each detector 20 including a number of detector elements 50 arranged in pack 51. Detectors 20 include pins 52 positioned within pack 51 relative to detector elements 50. Pack 51 is positioned on a backlit diode array 53 having a plurality of diodes 59. Backlit diode array 53 is in turn positioned on multi-layer substrate 54. Spacers 55 are positioned on multi-layer substrate 54. Detector elements 50 are optically coupled to backlit diode array 53, and backlit diode array 53 is in turn electrically coupled to multi-layer substrate 54. Flex circuits 56 are attached to face 57 of multi-layer substrate 54 and to DAS 32. Detectors 20 are positioned within detector assembly 18 by use of pins 52.

In the operation of one embodiment, X-rays impinging within detector elements 50 generate photons which traverse pack 51, thereby generating an analog signal which is detected on a diode within backlit diode array 53. The analog signal generated is carried through multi-layer substrate 54, through flex circuits 56, to DAS 32 wherein the analog signal is converted to a digital signal.

Figure 5:
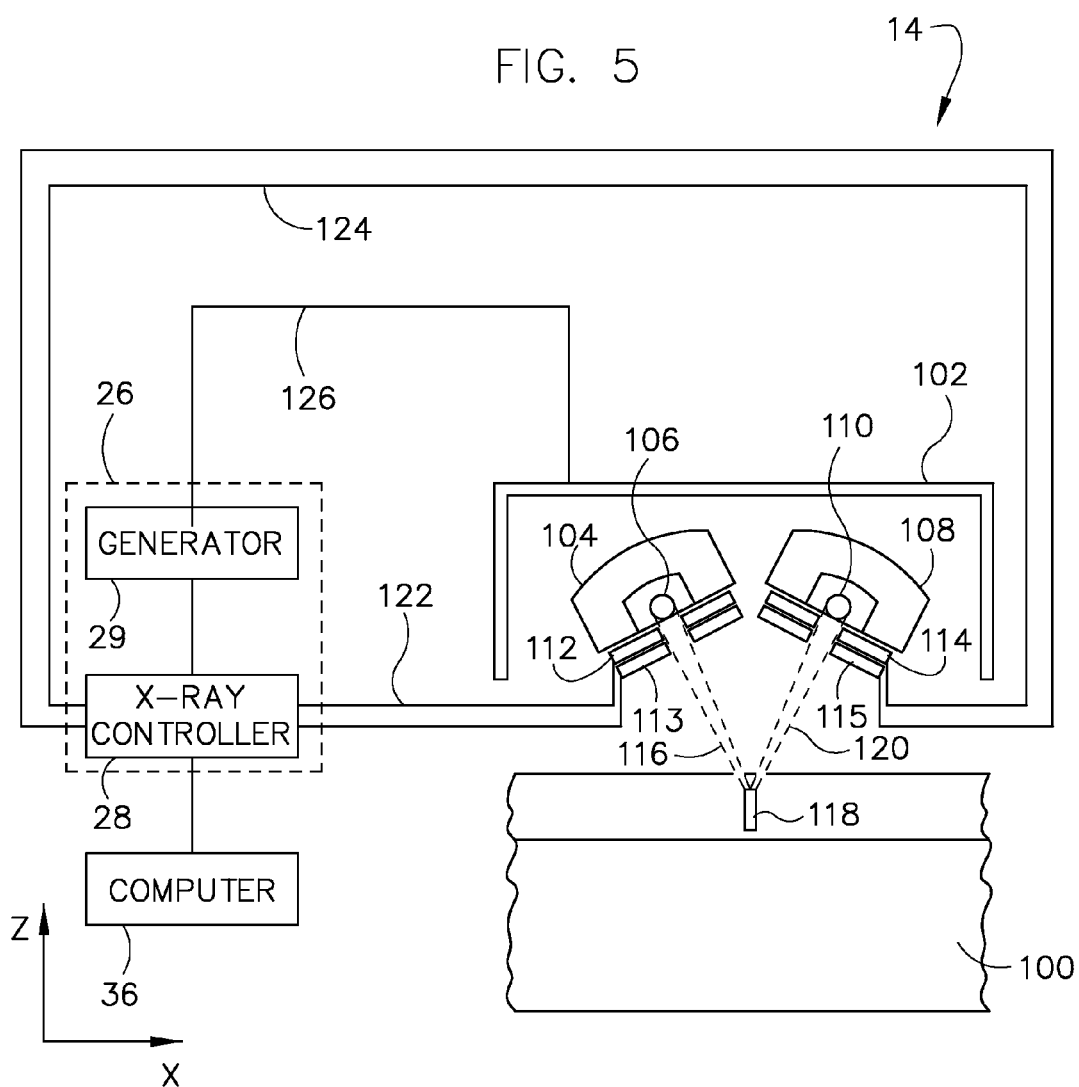
FIG. 5 is an illustration of a cathode assembly in an X-ray tube, the cathode assembly having two filaments emitting toward a focal spot of a target.

FIG. 5 illustrates parts of an embodiment of system 10 shown in FIGS. 1 and 2. System 10, as discussed, includes X-ray source 14, controller 26 that includes X-ray controller 28 and generator 29, and computer 36. X-ray source 14 includes a target 100 (illustrated from a point of view adjacent an edge of the target) and a cathode assembly 102, and having a gap formed therebetween. Cathode assembly 102 includes a first filament cup 104 having a first filament 106 and a second filament cup 108 having a second filament 110. Although filaments 106, 110 are illustrated as being the same size, one skilled in the art will recognize that first and second filaments 106, 110 need not be the same size but may be configured as one small and one large filament. In such fashion, the filaments may be sized, in one example, according to expected mA emission, and one filament may be designated for low tube voltage operation while the other may be designated for high tube voltage operation.

According to embodiments of the invention, each filament cup 104, 108 includes an ability to grid their respective filaments 106, 110. The ability to grid the filaments, as understood in the art, typically includes applying a voltage that is slightly negative in voltage with respect to the filament such that electrons emitted from the filament are diverted to the grid, thus enabling electrons to be rapidly switched off from impacting the target. Because the voltage used to grid is typically on order of up to a few thousand volts, the response time is on the order of a micro-second or so, thus enabling quick and efficient modulation of tube current, otherwise designated in the art as mA. FIG. 5 includes an illustration of tube current or mA gridding electrodes that are positioned proximately to electron beams that emit from filaments 106, 110. However, other embodiments are equally applicable to include a one-dimensional grid positioned in the path of the electrons, as will be illustrated later.

First filament cup 104 includes a first pair of mA gridding electrodes 112 proximate first filament 106. Second filament cup 108, likewise, includes a second pair of mA gridding electrodes 114 proximate second filament 110. First filament 106 is positioned to emit a first beam of electrons 116 toward a focal spot 118, and second filament 110 is positioned to emit a second beam of electrons 120 toward focal spot 118. Each pair of gridding electrodes 112, 114 is configured to have a gridding voltage applied thereto. The mA gridding electrodes 112 of first filament 106 are coupled to X-ray controller 28 via a line 122, and mA gridding electrodes 114 of second filament 110 are coupled to X-ray controller 28 via a line 124. Generator 29 is coupled to cathode assembly 102 via a high voltage line 126. In such fashion, high and low tube voltage may be selectively, independently, and alternatingly applied to cathode assembly 102 via high voltage line 126. Thus, energy applied to each filament 106, 110 may be selectively and independently controlled and applied via high voltage line 126 and via gridding electrodes 112, 114. One skilled in the art will recognize that the operation described herein need not be limited to a single X-ray tube configuration, but is applicable to any X-ray tube configuration. For instance, in one embodiment the X-ray tube may have a grounded anode, while in another embodiment the X-ray tube may operate in a bipolar arrangement having a positive voltage applied to a cathode and a negative voltage applied to an anode.

Gridding voltages applied to first and second mA gridding electrodes 112, 114 are typically between a few hundred volts and several thousand volts. It is to be understood that, although each pair of mA gridding electrodes 112, 114 is respectively illustrated as a pair of electrodes, the gridding electrodes may instead each be a single piece electrode. In other words, as an example, mA gridding electrode 112 may be a single piece having an opening or aperture therein and through which electrons pass toward focal spot 118. It is also to be understood that in addition to each grid, there maybe additional focusing and deflection electrodes to cause further focusing and deflection thereof. This provides a capability to compensate the focal spot and location shift that can result from operating two beams at the same time.

In operation, cathode assembly 102 of X-ray tube 14 is able to provide a wide dynamic range of mA according to embodiments of the invention. On a low end of the dynamic range, one of the first and second beams of electrons 116, 120 may be entirely gridded off via a respective first and second pair of mA gridding electrodes 112, 114, while the other of the first and second beams of electrons 116, 120 may be fully on or partially or fully gridded off via the other of the respective first and second pair of mA gridding electrodes 112, 114. As such, as a tube voltage or energy level is rapidly switched from a low voltage to a high voltage level, mA or filament emission to focal spot 118 may be correspondingly controlled via gridding voltages that substantially cut emission from one or both of the filaments. In such fashion, emission to focal spot 118 may be cut to zero mA, or to a low mA such as 5 mA, for example.

At the other end or high end of dynamic range of mA, both beams of electrons 116, 120 may be caused to simultaneously emit toward focal spot 118 in order that the total mA exceeds, for instance, 1000 mA. As understood in the art, each beam of electrons 116, 120 may be maximized by maximizing an operating temperature of each respective filament 106, 110. Further, total mA at focal spot 118 may be variably or infinitely controlled by selectively controlling focusing voltages applied to each possible focusing electrode which is located at grid electrodes 112, 114. As such, a complete dynamic range from zero mA (both filaments 106, 110 fully gridded) to full mA (maximum emission from each filament 106, 110, no gridding) may be realized according to embodiments of the invention. Thus, as tube voltage is rapidly switched from a high tube voltage to a low tube voltage, total focal spot mA may likewise be rapidly modulated to a corresponding low mA and high mA, as desired. Thus, a total mA may be emitted to focal spot 118 from a combined set of filaments 106, 110 in such a fashion that high mA may be realized.

Due to the space charge, two beams will affect each other when both beams are turned on. This will either shift the location of the beam or the focal spot size of the beam. The shift of location and/or focal spot size can be characterized either via simulation or experimental measurement. One way to compensate this shift is to calibrate and compensate the effects during image reconstruction for CT. Another way to compensate this is to have a mechanism such that a position and/or shape of each electron beam 116, 120 may be independently controlled. This can be achieved via respective focusing and deflecting electrodes 113, 115 that may be optionally positioned proximate the gridding electrodes 112, 114. By doing this, position and/or shape of each may be independently controlled so that both their position and shape overlap to form focal spot 118. In one embodiment, each pair of focusing and deflecting electrodes may be decoupled from one another such that a differential voltage may be applied thereto. Thus, additional electrodes 113, 115 may be provided near each filament 106, 110 to provide functionality as understood in the art. In other words, pairs of electrodes 112, 114 as illustrated may provide multiple functionality to include mA modulation, beam shaping, and beam location when used to form focal spot 118. However, multiple electrodes 113, 115 may be provided to separately and independently control focal spot location, gridding, length, width, deflection, and shape control, as understood in the art. As such, image reconstruction may be enhanced by compensating for focal spot shape, focal spot size, and the like, which may be independently adjusted using electrodes as discussed. Such compensation may take place after controller 28 of system 10 characterizes a focal spot shape, a focal spot size, or both, and then adjusting voltages applied to the electrodes, accordingly.

Emission from each filament 106, 110 may be modulated, for example, according to the following embodiments. In one embodiment, both filaments 106, 110 may be set to a maximum filament temperature, and then separately modulated via gridding electrodes 112, 114 as described above. In such fashion and as described, total mA emitted to focal spot 118 may dynamically range from approximately zero mA to a maximum (when both filaments 106, 110 are not gridded) that may exceed 1000 mA, limited only by a maximum temperature set point of each filament 106, 110. Thus, maximum mA may be achieved for extremes of operation (1000 mA or greater) while enabling mA modulation speeds that are limited only by, for instance, an ability to provide gridding voltages to respective pairs of electrodes 112, 114 (typically on order of 1 microsecond, as an example).

In another embodiment, one filament may be set to a maximum filament temperature and the other filament may be set to a fraction of its maximum temperature. The maximum temperature may be selected based on a desired mA at low tube voltage, and the fraction of maximum temperature may be selected based on a desired mA at high tube voltage, as examples. In such fashion, gridding voltages may be applied in conjunction with fast switching of low and high tube voltage, and gridding operation may be a simple on-off operation, thus enabling responsive mA modulation on the order of microseconds and in conjunction with fast tube voltage switching.

According to one embodiment, the filaments may be sized to correspond to a low kVp and a high kVp operation, and corresponding emission of filaments 106, 110. Thus, the filaments 106, 110 may be continuously maintained at a maximum temperature and then separately gridded in correspondence with low and high tube voltage switching. As one example, first filament 106 may be a small filament relative to second filament 110. As such, first filament 106 may be set to a temperature that corresponds to high tube voltage/low mA operation, and second filament 110 may be set to a temperature that corresponds to a low tube voltage/high mA operation. Thus, as switching occurs from low to high tube voltage, gridding may be correspondingly controlled. Thus, filaments may be properly sized based on expected mA, focal spot size, shape, and deflection abilities, as examples and as understood in the art. Further, this embodiment also enables extremes of mA emission, as described, to achieve full dynamic range from approximately zero mA to 1000 mA or greater, while allowing quick and efficient mA modulation in conjunction with fast tube voltage switching.

Figure 6:
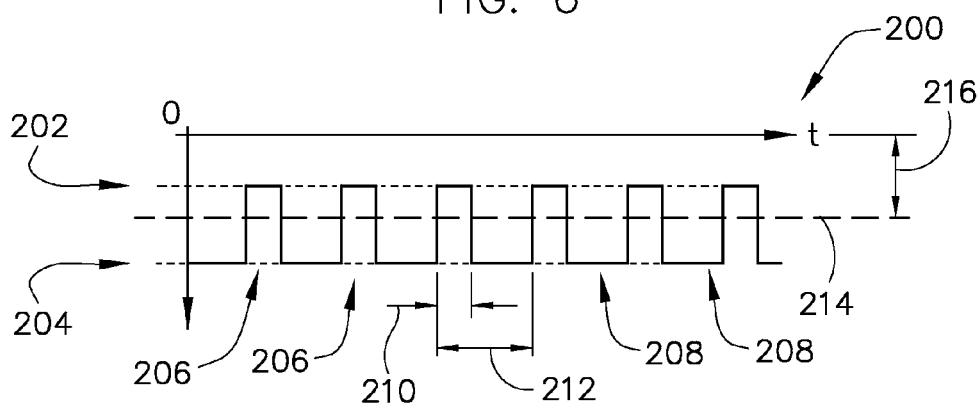
FIG. 6 is a graphical illustration of a duty cycle for gridding operation of a cathode assembly.

According to another embodiment, emission and mA modulation may be controlled via a duty cycle control scheme. In this operation, each filament 106, 110 is set to, for instance, maximum emission, and one or both pairs of gridding electrodes may be connected to a train of fast voltage pulses, as can be seen in FIG. 6. Referring to FIG. 6, a train of voltage pulses 200 ranging from a first negative voltage 202 to a second negative voltage 204 may be applied to gridding electrodes 112, 114. The train of voltage pulses 200 includes a first set of pulses 206 at the first negative voltage 202 and a second set of pulses 208 at the second negative voltage 204. Each pulse of the first set of pulses 206 includes a pulse width 210, and the pulses 206 are set in a repeating pattern of pulses over a repeating cycle 212 as illustrated. The pulses 206, 208 result in an average voltage 214, having a magnitude 216, the magnitude 216 based on first and second negative voltages 202, 204, pulse width 210, and a total time of repeating cycle 212. One skilled in the art will recognize that the average voltage 214 illustrated may be thus generally expressed as a function of a duty cycle. Thus, one skilled in the art will recognize that application of train of voltage pulses 200 to an electrode results in a resultant mA that may be expressed generally as a function of peak mA and a duty cycle, taking into account widths of pulses 206, 208, and also taking into account a peak negative voltage 204 and a "valley" voltage 202. For instance and as one example, an average mA may be expressed as a function of 1) duty cycle of second set of pulses 208 times second negative voltage 204, plus 2) one minus duty cycle of second set of pulses 208 times first negative voltage 202.

Although X-ray tube 14 is illustrated in FIG. 5 as having two filaments 106, 110 illustrated therein and positioned to emit respective first and second beams of electrons 116, 120 toward focal spot 118, it is to be understood that one or multiple additional filaments may be included that can all be positioned to direct a respective electron beam toward focal spot 118. Thus, consistent with that described herein, each filament may be positioned in a respective filament cup within a cathode assembly such that a plurality of electron beams are directed toward focal spot 118. In one embodiment (not illustrated), ten filaments are positioned within a cathode assembly, such as cathode assembly 102 of FIG. 5 such that each emits a respective electron beam toward focal spot 118.

Train of voltage pulses 200 may be applied to a gridding electrode. As such, emission from a filament may be controlled, accordingly. In one example, a CT acquisition view window of 200 microseconds may have a gridding electrode controlled via a pulse train having multiple cycles therein, thus a response time may be on order of microseconds when controlling voltage applied to gridding electrodes as discussed.

Figure 7:
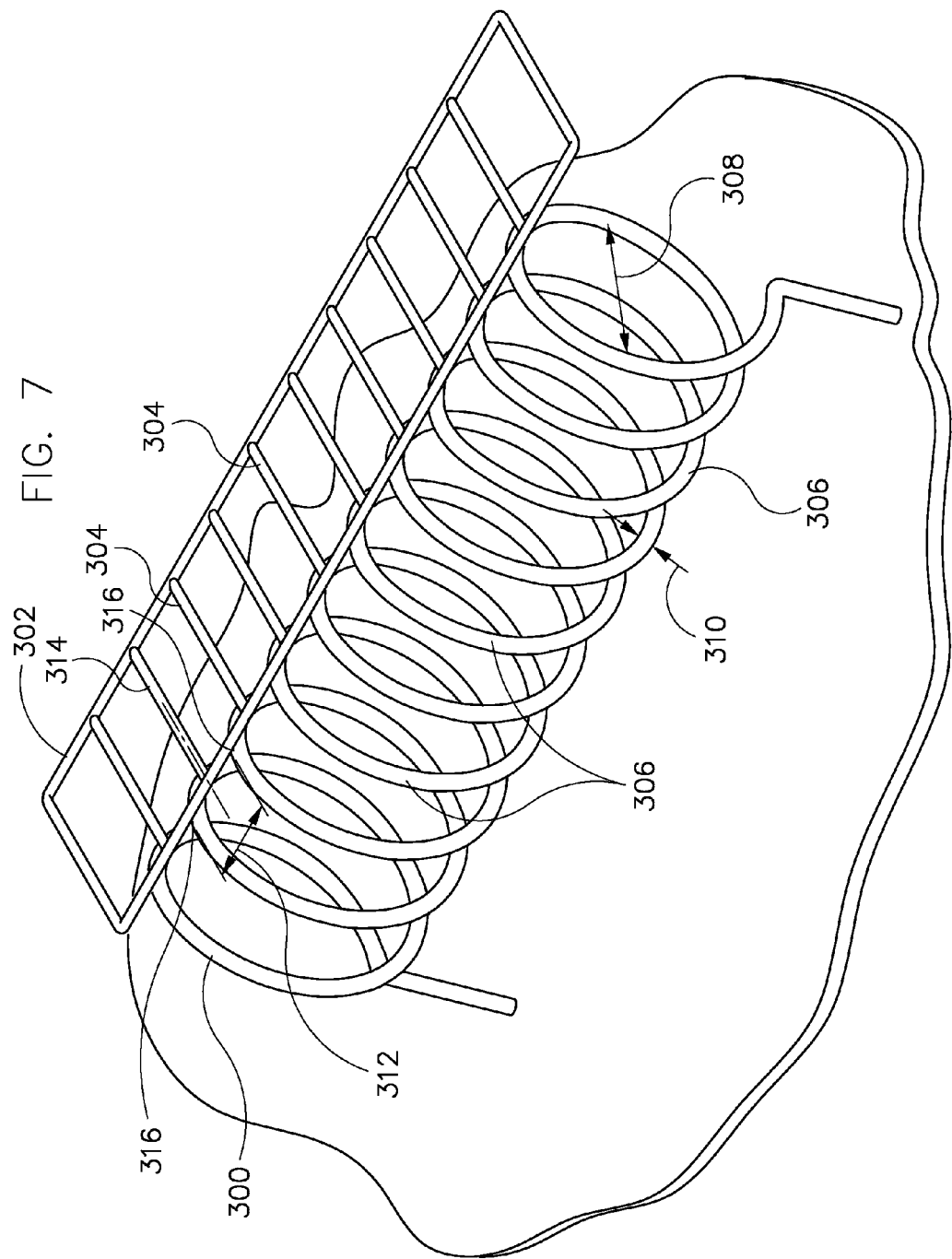
FIG. 7 is a perspective view of a filament having a one-dimensional gridding electrode coupled thereto.

A one-dimensional gridding electrode may be used to grid mA emission, in lieu of a pair of gridding electrodes such as electrodes 112 or 114, as discussed. Referring now to FIG. 7, a filament 300, such as filament 106 or 110 of FIG. 5, may be gridded by placing a one-dimensional (1D) grid 302 near filament 300, according to embodiments of the invention. As with gridding electrodes 112, 114 above, a gridding voltage may be applied to 1D grid 302 using either an on-off operation or a duty cycle. As such, mA from filament 300 may be controlled via a voltage applied to 1D grid 302 as described. According to one embodiment, rungs 304 of 1D grid 302 may be positioned to minimally affect emission from filament 300. As known in the art, emission from filament 300 is not uniform from each filament coil 306, but is a function of a number of design and operating parameters, including but not limited to a coil diameter 308, a filament rung diameter 310, and a kV applied to the filament, as examples. A profile of electron emission from filament 300 may be determined empirically or by computer model, as examples, based on such design and operating parameters, which may be used to determine where emission is minimal as a function of a location of each rung 306. Based on the determined profile of electron emission, the 1D grid 302 may be positioned with respect to filament 300 such that emission therefrom is minimally impacted when voltage is not applied to 1D grid 302. As an example, in an embodiment where minimal emission occurs at a location equidistant between rungs 312, 1D grid 302 is positioned such that a respective rung 314 is placed at the minimal emission location equidistant between the corresponding rungs 316. In another embodiment, rungs 316 are not positioned equidistant between coils 306 but are instead positioned offset axially therefrom and at a location having minimal emission, as determined empirically or by computer model, as discussed. In yet another embodiment, 1D grid 302 may be positioned such that an imaginary planar surface formed by rungs 314 is generally perpendicular to electrons as they pass between rungs 314. However, the invention is not to be so limited, and 1D grid 302 may be positioned such that rungs 314 have a tilt or cant and are not generally perpendicular to electrons as they pass between rungs 314, but are tilted by a few degrees or more.

Accordingly, 1D grid 302 may be selectively placed to minimally impact emission of electrons during emission therefrom, while providing an ability to grid mA as discussed.

Figure 8:
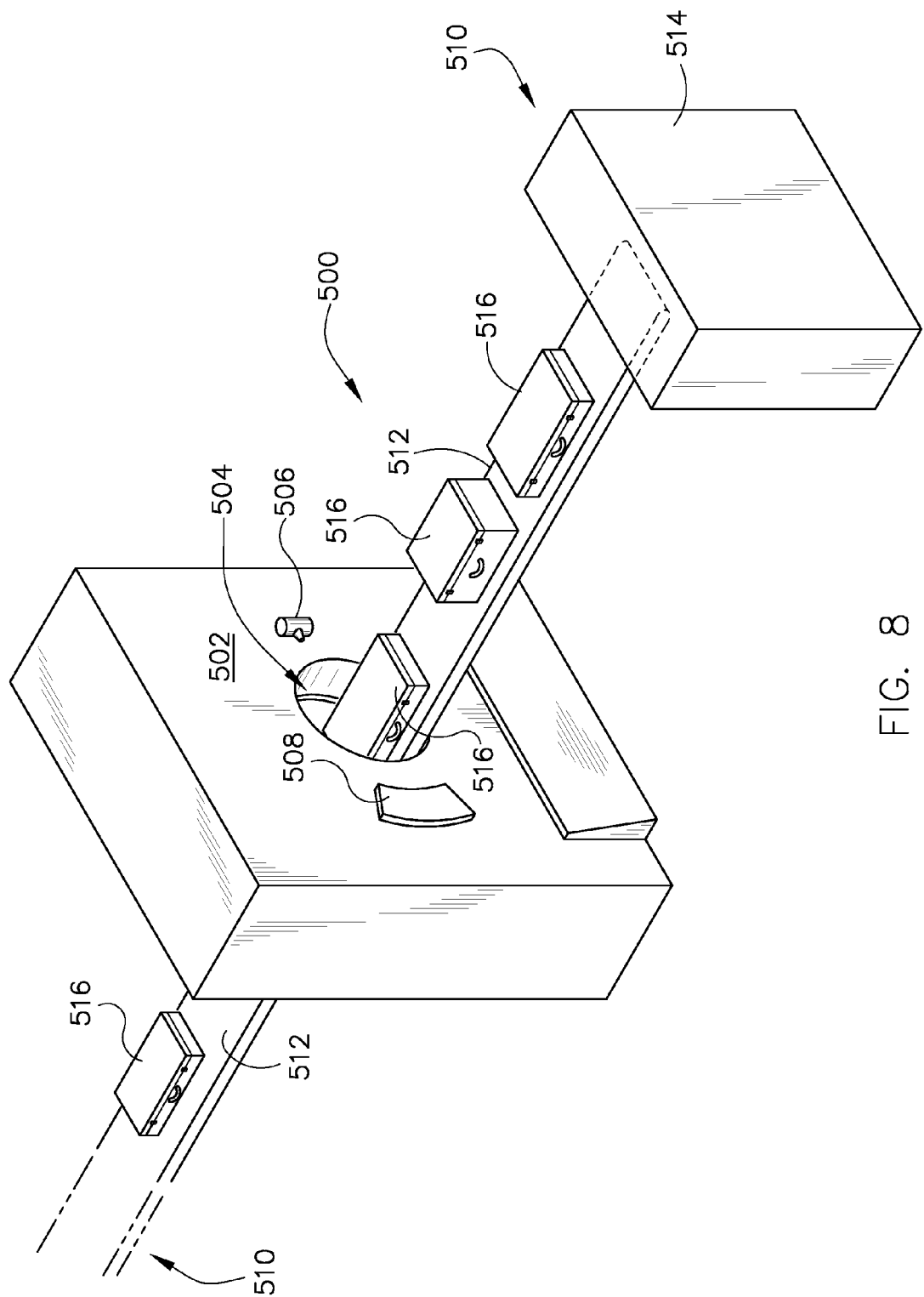
FIG. 8 is a pictorial view of an X-ray system for use with a non-invasive package inspection system that can benefit from incorporation of an embodiment of the invention.

FIG. 8 is a pictorial view of an X-ray system 500 for use with a non-invasive package inspection system. The X-ray system 500 includes a gantry 502 having an opening 504 therein through which packages or pieces of baggage may pass. The gantry 502 houses a high frequency electromagnetic energy source, such as an X-ray tube 506, and a detector assembly 508. A conveyor system 510 is also provided and includes a conveyor belt 512 supported by structure 514 to automatically and continuously pass packages or baggage pieces 516 through opening 504 to be scanned. Objects 516 are fed through opening 504 by conveyor belt 512, imaging data is then acquired, and the conveyor belt 512 removes the packages 516 from opening 504 in a controlled and continuous manner. As a result, postal inspectors, baggage handlers, and other security personnel may non-invasively inspect the contents of packages 516 for explosives, knives, guns, contraband, etc. One skilled in the art will recognize that gantry 502 may be stationary or rotatable. In the case of a rotatable gantry 502, system 500 may be configured to operate as a CT system for baggage scanning or other industrial or medical applications.

A technical contribution for the disclosed method and apparatus is that it provides for a computer implemented control of electron beam emission.

According to one embodiment of the invention, an X-ray tube includes a target and a cathode assembly. The cathode assembly includes a first filament configured to emit a first beam of electrons toward the target, a first gridding electrode coupled to the first filament, a second filament configured to emit a second beam of electrons toward the target, and a second gridding electrode coupled to the second filament.

In accordance with another embodiment of the invention, a method of multi-energy imaging includes determining a first X-ray tube current based on a first X-ray tube voltage level, and a second X-ray tube current based on a second X-ray tube voltage level, applying a first filament current to a first filament, and a second filament current to a second filament, alternatingly applying the first X-ray tube voltage level and the second X-ray tube voltage level to a cathode assembly that houses the first filament and the second filament, selectively applying first and second gridding voltages to respective first and second gridding electrodes during application of the first and second X-ray tube voltage levels across a cathode-anode gap such that emission from the first and second filaments is separately controllable respective to the tube voltage, acquiring imaging information from X-rays generated at a focal spot, and generating an image using the imaging information.

In accordance with yet another embodiment of the invention, an imaging system includes a gantry having an opening for receiving an object to be scanned, and an X-ray source coupled to the gantry and configured to project X-rays through the opening. The X-ray source includes a target and a cathode assembly. The cathode assembly includes a first filament configured to emit a first electron beam toward the target, a first gridding electrode coupled to the first filament, a second filament configured to emit a second electron beam toward the target, and a second gridding electrode coupled to the second filament. The system includes a controller configured to acquire imaging data from X-rays generated by electrons emitted from the cathode assembly during energization of the cathode assembly to a first tube voltage level and a second tube voltage level, and generate an image using the acquired imaging data.

Embodiments of the invention have been described in terms of the preferred embodiment(s), and it is recognized that equivalents, alternatives, and modifications, aside from those expressly stated, are possible and within the scope of the appending claims.

What is claimed is:

1. An X-ray tube comprising:
    a target; and
    a cathode assembly comprising:
        a first filament configured to emit a first beam of electrons toward the target;

a first gridding electrode coupled to the first filament, wherein the first gridding electrode comprises a one-dimensional mesh comprising a plurality of rungs, and wherein each rung of the plurality of rungs is aligned with a respective gap between windings of the first filament;
a second filament configured to emit a second beam of electrons toward the target; and
a second gridding electrode coupled to the second filament.

2. The X-ray tube of claim 1 wherein the cathode assembly is configured to have selectively applied a first gridding voltage to the first gridding electrode via a first lead and a second gridding voltage to the second gridding electrode via a second lead.

3. The X-ray tube of claim 2 wherein the cathode assembly is configured to have the first and second gridding voltages selectively applied to control emission of the first and second beams of electrons to achieve a first desired emission when a first tube voltage is applied across a gap between the cathode assembly and the target, and to achieve a second desired emission when a second tube voltage is applied across the gap between the cathode assembly and the target.

4. The X-ray tube of claim 1 wherein the emission from the first and second filaments occurs simultaneously to form a focal spot on the target.

5. The X-ray tube of claim 1 further comprising at least one additional filament configured to emit an additional beam of electrons toward the target and at least one additional gridding electrode coupled to the additional filament.

6. The X-ray tube of claim 1 wherein the cathode assembly is configured such that emission is from only one of the first filament and the second filament.

7. The X-ray tube of claim 1 wherein the second gridding electrode is independently controllable from the first gridding electrode.

8. The X-ray tube of claim 1 wherein the first filament and the second filament are positioned to emit the first beam of electrons and the second beam of electrons toward a predetermined location, wherein both beams impact at the same focal spot location on the target.

9. The X-ray tube of claim 1 further comprising one of a focusing and deflection electrode positioned proximate to a respective gridding electrode and biased with a respective voltage when each respective beam of electrons is not gridded off.

10. The X-ray tube of claim 1 wherein the cathode assembly is configured such that a tube voltage level applied thereto is applied to both the first filament and the second filament.

11. A method of multi-energy imaging comprising:
determining a first X-ray tube current based on a first X-ray tube voltage level, and a second X-ray tube current based on a second X-ray tube voltage level;
applying a first filament current to a first filament, and a second filament current to a second filament;
alternatingly applying the first X-ray tube voltage level and the second X-ray tube voltage level to a cathode assembly that houses the first filament and the second filament;
selectively applying first and second gridding voltages to respective first and second gridding electrodes during application of the first and second X-ray tube voltage levels across a cathode-anode gap such that emission from the first and second filaments is separately controllable respective to the tube voltage, wherein the first gridding electrode comprises a one-dimensional mesh comprising a plurality of rungs, and wherein each rung of the plurality of rungs is aligned with a respective gap between windings of the first filament;
acquiring imaging information from X-rays generated at a focal spot; and
generating an image using the imaging information.

12. The method of claim 11 wherein selectively applying the first and second gridding voltages comprises selectively applying the first and second gridding voltages such that emission from the first and second filaments occurs simultaneously.

13. The method of claim 12 wherein selectively applying the first and second gridding voltage comprises modulating one of the first and second gridding voltages with a duty cycle.

14. The method of claim 13 wherein the first X-ray tube voltage level is different from the second X-ray tube voltage level.

15. The method of claim 14 wherein the first X-ray tube current is different from the second X-ray tube current.

16. An imaging system comprising:
a gantry having an opening for receiving an object to be scanned;
an X-ray source coupled to the gantry and configured to project X-rays through the opening, the X-ray source comprising:
a target; and
a cathode assembly comprising:
a first filament configured to emit a first electron beam toward the target;
a first gridding electrode coupled to the first filament, wherein the first gridding electrode comprises a one-dimensional mesh comprising a plurality of rungs, and wherein each rung of the plurality of rungs is aligned with a respective gap between windings of the first filament;
a second filament configured to emit a second electron beam toward the target; and
a second gridding electrode coupled to the second filament; and
a controller configured to:
acquire imaging data from X-rays generated by electrons emitted from the cathode assembly during energization of the cathode assembly to a first tube voltage level and a second tube voltage level; and
generate an image using the acquired imaging data.

17. The imaging system of claim 16 wherein the first filament and the second filament are positioned to emit the first electron beam and the second electron beam toward a same focal spot location on the target.

18. The imaging system of claim 16, wherein the controller is further configured to:
set the first filament to achieve a first emission and the second filament to achieve a second emission;
energize the cathode assembly to the first tube voltage level and to the second tube voltage level;
apply a first gridding voltage to the first gridding electrode in conjunction with energization of the cathode assembly to the first tube voltage level;
apply a second gridding voltage to the second gridding electrode in conjunction with energization of the cathode assembly to the second tube voltage level;
acquire imaging data from X-rays generated by electrons emitted from the cathode assembly during energization of the cathode assembly to the first and second tube voltage levels; and
generate an image using the acquired imaging data.

19. The imaging system of claim 1 wherein the controller is further configured to selectively apply the first gridding voltage to the first gridding electrode and a second gridding voltage to the second gridding electrode such that emission from the first and second filaments occurs simultaneously to form a focal spot on the target.

20. The imaging system of claim 19 wherein the controller is further configured to:
   characterize one of a focal spot shape and a focal spot size; and
   compensate image reconstruction based on the characterization.

21. The imaging system of claim 18 wherein the controller is further configured to:
   determine a first desired emission level based on the first tube voltage level;
   determine a second desired emission based on the second tube voltage level; and
   selectively apply gridding voltages to the first and second gridding electrodes to control emission of the first and second electron beams to achieve the first desired emission level from the first filament when the first energy level is applied, and to achieve the second desired emission from the second filament when the second energy level is applied.

22. The imaging system of claim 18 wherein the controller is further configured to set the first temperature of the first filament to a first desirable emission level, and to set the second temperature of the second filament to a second desirable emission level.

23. The imaging system of claim 18 further comprising a generator configured to apply both the first tube voltage level and the second energy level to the cathode assembly, wherein the second voltage level is greater than the first energy level.

24. The imaging system of claim 23 wherein the first tube voltage level is greater than the second tube voltage level.

25. The imaging system of claim 18 wherein the controller is further configured to modulate emission of one of the first and second electron beams by being configured to modulate the applied first gridding voltage to the first gridding electrode via a duty cycle.

* * * * *